(12) United States Patent
Hart et al.

(10) Patent No.: US 10,006,978 B2
(45) Date of Patent: Jun. 26, 2018

(54) METHOD AND SYSTEM FOR SIGNAL PROCESSING

(71) Applicant: LEIDOS INNOVATIONS TECHNOLOGY, INC., Gaithersburg, MD (US)

(72) Inventors: Corey Brendan Hart, Philadelphia, PA (US); William J. Rose, Wayne, PA (US)

(73) Assignee: LEIDOS INNOVATIONS TECHNOLOGY, INC., Gaithersburg, MD (US)

(*) Notice: Subject to any disclaimer, the term of this patent is extended or adjusted under 35 U.S.C. 154(b) by 11 days.

(21) Appl. No.: 14/725,833

(22) Filed: May 29, 2015

(65) Prior Publication Data

US 2015/0346302 A1    Dec. 3, 2015

Related U.S. Application Data

(60) Provisional application No. 62/005,285, filed on May 30, 2014.

(51) Int. Cl.

| | |
|---|---|
| G01N 33/48 | (2006.01) |
| G01R 33/54 | (2006.01) |
| A61B 5/055 | (2006.01) |
| G06F 19/24 | (2011.01) |
| G06T 7/00 | (2017.01) |
| G06N 3/04 | (2006.01) |
| G06G 7/58 | (2006.01) |

(52) U.S. Cl.
CPC .............. *G01R 33/54* (2013.01); *A61B 5/055* (2013.01); *G06F 19/24* (2013.01); *G06N 3/049* (2013.01); *G06N 3/0454* (2013.01); *G06T 7/0016* (2013.01); *G06T 2207/10088* (2013.01); *G06T 2207/20084* (2013.01); *G06T 2207/30016* (2013.01)

(58) Field of Classification Search
CPC .......... G06F 19/18; G06F 19/20; G06F 19/22; G06F 19/24; G06F 19/32; G06F 19/322
See application file for complete search history.

(56) References Cited

U.S. PATENT DOCUMENTS

| | | |
|---|---|---|
| 2013/0116540 A1 | 5/2013 | Li et al. |
| 2014/0143193 A1 | 5/2014 | Zheng et al. |

FOREIGN PATENT DOCUMENTS

| | | |
|---|---|---|
| WO | WO 01/74240 A2 | 10/2001 |
| WO | WO 01/74240 A3 | 10/2001 |
| WO | WO 2007/061807 A2 | 5/2007 |
| WO | WO 2007/061807 A3 | 5/2007 |
| WO | WO 2011/115956 A1 | 9/2011 |
| WO | WO 2015/030606 A2 | 3/2015 |

OTHER PUBLICATIONS

Hart, C.B. et al.; Visual Feature Extraction From Voxel-Weighted Averaging of Stimulus Images in 2 fMRI Studies; Biomedical Engineering, IEEE Transactions on (vol. 60, Issue: 11); Jun. 13, 2013.

William John Rose, et al.; Visual Feature Extraction Methods and Systems; Co-pending U.S. Appl. No. 14/167,536, filed Jan. 29, 2014.

International Search Report and Written Opinion dated Sep. 8, 2015 in PCT/US2015/033287.

Tamer Olmez, et al., "MR Image Classification by the Neural Network and the Genetic Algorithms" 18th Annual International Conference of the IEEE Engineering in Medicine and Biology Society, XP000788303, 1996, 2 Pages.

*Primary Examiner* — Eric S DeJong
(74) *Attorney, Agent, or Firm* — Oblon, McClelland, Maier & Neustadt, L.L.P.

(57) ABSTRACT

Aspects of the disclosure provide a system for signal processing. The system includes a selection circuitry and a coordination detection circuitry. The selection circuitry is configured to receive data sets sampled at different time for a subject and select a plurality of data units from each data set that corresponds to regions of interests in the data set. The coordination detection circuitry is configured to receive the selected data units corresponding to the regions of interests over time, and detect a coordination of the regions of interests over time.

16 Claims, 5 Drawing Sheets

METHOD AND SYSTEM FOR SIGNAL PROCESSING

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

In the US, each year, traumatic brain injuries (TBI) affect almost 2 million, with 75% of those being mild TBI. Current methods to detect traumatic brain injuries rely on questionnaires, which are focused on changes in the psychological, physical, and/or behavioral aspects of the patient.

SUMMARY

Aspects of the disclosure provide a system for signal processing. The system includes a selection circuitry and a coordination detection circuitry. The selection circuitry is configured to receive data sets sampled at a constant time interval for a subject and select a plurality of data units from each data set that corresponds to informational channels in the data set. The coordination detection circuitry is configured to receive the selected data units corresponding to the informational channels over time, and detect a coordination of the informational channels over time.

According to an aspect of the disclosure, the selection circuitry is configured to receive voxels activity at the different time. In an embodiment, the selection circuit is configured to receive the voxel activity or activity of regions-of-interest extracted from voxels recorded from functional magnetic resonance imaging (fMRI) of the subject. In an example, the subject's fMRI activity is recorded during resting state activity.

According to another aspect of the disclosure, the coordination detection circuitry is configured to input the plurality of data units at the different time into a spiking neural network to drive neurons in the spiking neural network. In an embodiment, the spiking neural network outputs a weight matrix for the neurons based on activities of the neurons. Then, the coordination detection circuitry is configured to calculate an eigenvector of the weight matrix. Further, the coordination detection circuitry is configured to compare a portion of the eigenvector with a baseline to determine a feature of the subject.

In another embodiment, the spiking neural network outputs spike trains indicative of activities of the neurons. In an example, the spike trains are input to another spiking neural network. In another example, the spike trains are feedback to the spiking neural network.

Aspects of the disclosure provide a method for signal processing. The method includes receiving, by an interface circuitry, data sets sampled at different time for a subject, selecting, by a selection circuitry, a plurality of data units from each data set, the data units corresponding to informational channels (e.g., regions of interests) in the data set, and detecting, by a coordination detection circuitry, a coordination of the informational channels over time.

BRIEF DESCRIPTION OF THE DRAWINGS

Various embodiments of this disclosure that are proposed as examples will be described in detail with reference to the following figures, wherein like numerals reference like elements, and wherein.

DETAILED DESCRIPTION OF EMBODIMENTS

The disclosed methods and systems below may be described generally, as well as in terms of specific examples and/or specific embodiments. For instances where references are made to detailed examples and/or embodiments, it is noted that any of the underlying principles described are not to be limited to a single embodiment, but may be expanded for use with any of the other methods and systems described herein as will be understood by one of ordinary skill in the art unless otherwise stated specifically.

A "voxel" is a three dimensional pixel residing at a particular (Y, Y, Z) coordinate and having one or more descriptive values, such as intensity. Raw functional Magnetic Resonance Imaging (fMRI) image data of the human brain can now be characterized by a large number of voxels.

Figure 1:
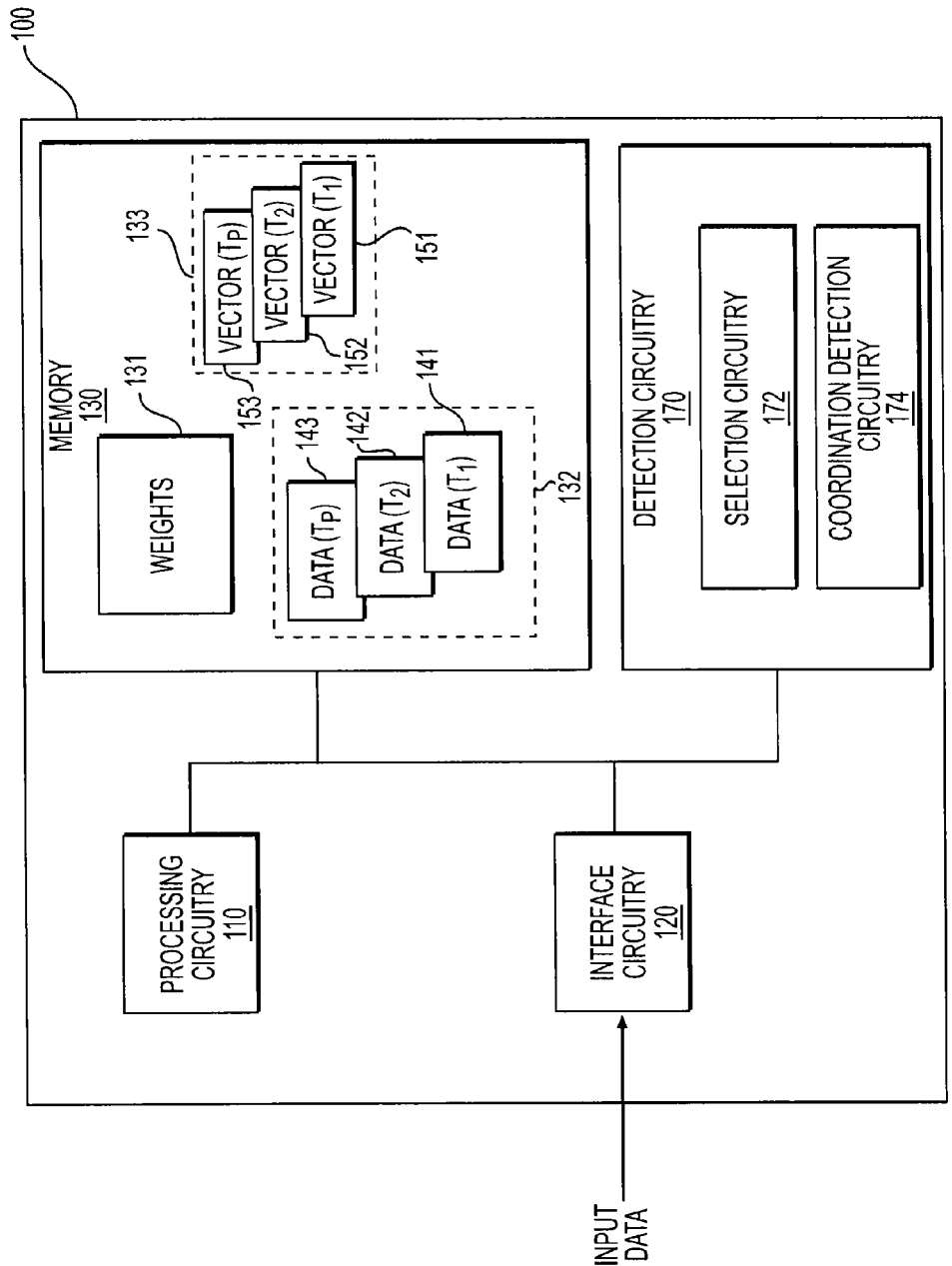
FIG. 1 shows a block diagram of an exemplary system 100 according to an embodiment of the disclosure.

FIG. 1 shows a block diagram of an exemplary system 100 according to an embodiment of the disclosure. The system 100 is configured to receive data sets sampled at different time for a subject and detect a coordination of regions of interests from the data sets.

The system 100 can be used in various applications. In an example, the system 100 is an image processing system 100 configured to process fMRI brain images taken at different time, detect a coordination of different regions of the brain for a function, and to detect changes in brain status, such as mild traumatic brain injury, and the like based on the detected coordination. In another example, the system 100 is a geographic analysis system 100 configured to receive geographic images taken at different time, and to detect geographic changes over time. In another example, the system 100 is a syntax analysis system 100 configured to receive text information on a website at different time, and detect syntax changes over time. In another example, the system 100 is a traffic analysis system 100 configured to receive traffic images taken at different time, and to detect traffic changes over time.

In the FIG. 1 example, the system 100 includes a processing circuitry 110, an interface circuitry 120, a memory 130 and a detection circuitry 170. These elements are coupled together by a bus as shown in FIG. 1. It is noted that although a bussed architecture is depicted in the example of FIG. 1, in other embodiments any or all of the various functional components may be realized in other forms. In an example, the detection circuitry 170 can be realized using dedicated processing electronics interconnected by separate control and/or data buses embedded in one or more Application Specific Integrated Circuits (ASICs). In another example, the detection circuitry 170 is integrated with the processing circuitry 110.

The interface circuitry 120 is configured to interface the system 100 with other suitably device, such as a camera, a network server, a MRI device, and the like to receive input data at different time. In an example, the input data is sent to the system 100 as data sets. Each data set corresponds to input data at a time. The data set includes a plurality of data points. In an example, a data set for fMRI includes a plurality of voxels of the subject recorded at a time.

In an embodiment, the processing circuitry 110 is configured to provide control signals to other components of the system 100 to instruct the other component to perform desired functions, such as processing the received data sets, detecting a coordination of regions of interests, and the like.

The memory 130 can include one or more storage media that provide memory space for various storage needs. In an example, the memory 130 stores code instructions to be executed by the processing circuitry 110 and stores data to be processed by the processing circuitry 110 and the detection circuitry 170. In another example, the memory 130 includes memory spaces allocated for system storage, and includes memory spaces allocated for user storage.

The storage media include, but are not limited to, hard disk drive, optical disc, solid state drive, read-only memory (ROM), dynamic random access memory (DRAM), static random access memory (SRAM), flash memory, and the like.

In the FIG. 1 example, a memory space 132 is allocated in the memory 130 to store the received data sets. In an example, the memory space 132 is large enough to store a plurality of data sets, such as data set 141 of time $T_1$, data set 142 of time $T_2$, data set 143 of time $T_P$. In another example, the memory space 132 is repetitively overwritten with a new data set when the new data set is received. Further, a memory space 133 is allocated to store vectors, such as vector 151 of time $T_1$, vector 152 of time $T_2$, vector 153 of time $T_P$. In an example, when a spiking neural network is used, the vectors correspond to spike trains output from neurons in the spiking neural network. For example, each vector includes outputs from neurons at a time. When a neuron fires at a time, the neuron outputs a binary value "1", and when the neuron does not fire at a time, the neuron outputs a binary value "0".

Further, in the example of using the spiking neural network, a memory space 131 is allocated to store weights for neurons in the spiking neural network. For example, a weight between a first neuron and a second neuron indicates an influence level of a neuron firing at the first neuron to the second neuron. In an example, the weights are stored in a form of a weight matrix.

According to an aspect of the disclosure, each data set includes a large number of data units. The large number of data units can be clustered into regions of interests. The detection circuitry 170 is configured to detect the coordination of the regions of interests from the data sets. In the FIG. 1 example, the detection circuitry 170 includes a selection circuitry 172 and a coordination detection circuitry 174. The selection circuitry 172 is configured to select data units in each data set that represent the regions of interests. Further, the coordination detection circuitry 174 is configured to detect the coordination of regions of interests from the selected data. It is noted that the regions of interests are referred to as information channels in an example.

In an embodiment, an activity at one of the regions of interests can cause changes in other regions of interests at a later time, and the relationship of the regions of interests is referred to as the coordination. The coordination detection circuitry 174 can detect the coordination of the regions of interests, and use the detected coordination in various applications.

In an example, traumatic brain injury (TBI) can cause certain level of behavioral deficits, even in cases where no structural damage is evident. In an embodiment, the coordination detection circuitry 174 can detect patterns of connectivity (e.g., coordination) during particular functional activity, and examine changes in connectivity of the brain regions to detect traumatic brain injury. For example, during a typical resting state, there exist correlations (e.g., coordination) between specific brain regions, and the correlations are referred to as default mode network (or task-negative network). Patterns of communication between distinct brain regions can change with for example, age, development, damage and the like. Further, the default mode network's activation is associated with attention and mind-wandering. Disruptions in its action may be associated with disruptions in attention characteristic of concussion-related damage. In an example, the coordination detection circuitry 174 is configured to detect patterns of communication between distinct brain regions to detect injury related disruptions of consciousness and use these disruptions as a metric for mild TBI detection.

It is noted various techniques can be used in the coordination detection circuitry 174 to detect the coordination of the regions of interests. In an embodiment, a spiking neural network is used to learn correlations between regions. In an example, neurons in the spiking neural network are connected with synapses that possess particular time delays in conduction, a given neuron pair can encode instantaneous correlations as well as any temporal correlations that occur up to some ceiling value, potentially increasing the complexity of patterns that can be encoded. Specifically, activations of regions of interests are used to drive dedicated neurons in this spiking neural network over their firing threshold and correlations between neural firing are encoded in a weight matrix. The weight matrix can be learned via an algorithm that is based on the spike time dependent plasticity. For example, a first neuron has a spike at time t1 and a second neuron has a spike at time t2. When the time difference between time t1 and time t2 is smaller than a threshold value, a weight from the first neuron to the second neuron is incremented; and when the time difference is larger than the threshold value, the weight is maintained. The weight matrix can be normalized to a maximum value of unity.

In an example, correlations between regions of interests can be fairly weak. In the example, a threshold is determined, and correlation values are compared with the threshold to generate a binary matrix. For example, the number of regions of interests is N, a binary matrix with N by N entries is generated. The binary matrix is similar to an adjacency matrix from graph theory, which describes the connectivity of nodes (e.g., regions of interests) in a network. Specifically, when a correlation value of a first region to a second region is larger than 0.1, a binary "1" is generated in the binary matrix at an entry with a first dimension corresponding to the first region and a second dimension corresponding to the second region; and when the correlation value is equal or smaller than 0.1, a binary "0" is generated in the binary matrix at the entry.

Further, in the example, techniques of spectral graph theory can be applied to the binary matrix. In an example, an eigenvector metric for nodes in the network can be calculated and used to determine coordination of the regions of interests.

During operation, in an example, the interface circuitry 120 receives data sets of voxels corresponding to fMRI for one or more baseline subjects (e.g., a person without brain injury, person diagnosed of certain level of brain injury) at different time. In an example, a data set includes 18,063 voxels recorded at a time. The selection circuitry 172 determines regions of interests, and selects voxels that represent the regions of interests. In an example, the selection circuitry 172 selects 21 regions of interests. The coordination detection circuitry 174 determines the coordination of the regions of interests based on the selected voxels. In an example, a spiking neural network includes 21 neurons, and the selected voxels are provided to the corresponding neurons as neuron activities via channels (e.g., information channels). Based on the neuron activities, the spiking neural network determines a spike train and a weight matrix. The spike train is used to classify the activity of the baseline subject (e.g., resting, reading), and the weight matrix is used to classify features and setup baseline features. In an example, multiple based line subjects are used to statistically setup a baseline feature.

Further, in an example, the interface circuitry 120 receives data sets of voxels corresponding to fMRI for a subject of potential brain injury. In an example, a data set includes 18,063 voxels recorded at a time. The selection circuitry 172 selects voxels that represent the regions of interests. The coordination detection circuitry 174 determines the coordination of the regions of interests based on the selected voxels. In an example, the selected voxels are provided to the spiking neural network as neuron activities. Based on the neuron activities, the spiking neural network determines a spike train and a weight matrix. The spike train is used to classify the activity of the baseline subject (e.g., resting, reading), and the weight matrix is compared with weight matrix of the baseline subject under the same activity to detect brain injury in an example.

In an experiment example, the system 100 is used to detect mild TBI under resting function. The system 100 achieves 90% correct detections and less than 10% false positives which is better than a psychological/behavioral based assessment of mild TBI that diagnoses based on headaches, ears ringing, altered/loss of consciousness, and dizziness/double vision.

Figure 2:
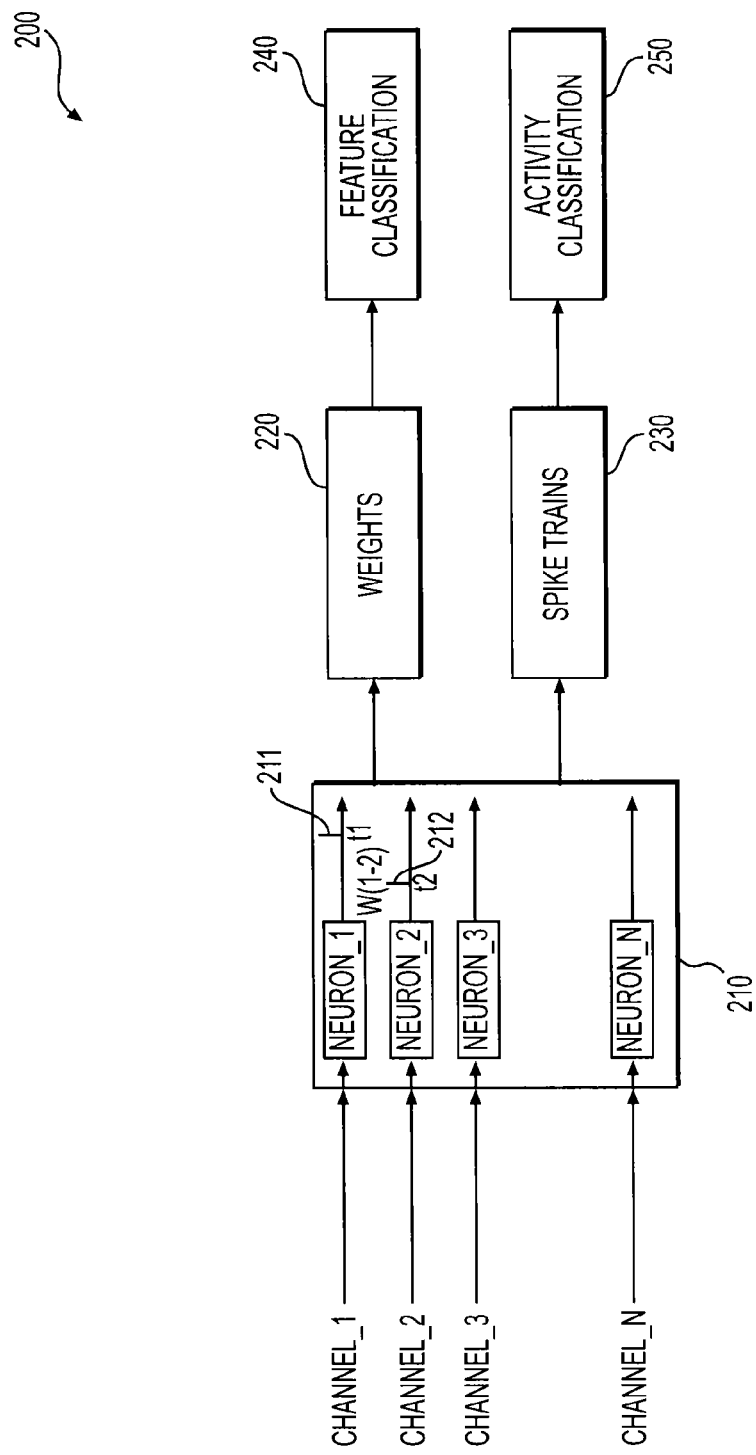
FIG. 2 shows an exemplary data flow 200 according to an embodiment of the disclosure.

FIG. 2 shows an exemplary data flow 200 according to an embodiment of the disclosure. In an example, the coordination detection circuitry 174 uses the data flow 200 for coordination detection. As shown in FIG. 2, a plurality of channels (e.g., CHANNEL_1 to CHANNEL_N) provide input data to a spiking neural network 210. The spiking neural network 210 includes a plurality of neurons (NEURON_1 to NEURON_N). The neurons receive the information from the channels and output spike trains. In an example, the information includes activities of regions of interests, and the activities of regions of interests are used to drive dedicated neurons in the spiking neuron network 210. When a neuron energy level is over a firing threshold, the neuron outputs a spike, otherwise the neuron outputs nothing. The output of the neuron can be represented by binary value, for example binary "1" is indicative of a spike, and binary "0" is indicative of no spike. Thus, each neuron outputs a spike train over time. At each time, the outputs of the neurons form a vector at the time. The vector can be suitably saved in the memory 130, such as the vectors 151-153 and the like. Based on the spike trains, in an example, the activities can be classified.

Further, according to an aspect of the disclosure, one neuron's activity can influence other neurons. In an example, the influence of one neuron's activity to another neuron is represented as weight. For example, the influence of NEURON_1 to NEURON_2 is represented by weight W(1-2).

In an example, the weight can be updated based on activities of the neurons. For example, NEURON_1 has a spike at time t1 as shown by 211, and the NEURON_2 has a spike at time t2 as shown by 212. When the time difference between time t1 and time t2 is smaller than a threshold value, the weight W(1-2) from NEURON_1 to NEURON_2 is incremented. Thus, based on the information received from the channels, the spike neuron network 210 can update the weights between the neurons, and output the updated weights. In an example, the weights are output in the form of a weight matrix. Based on the weight matrix, in an example, coordination features of the regions of interests can be classified.

Figure 3:
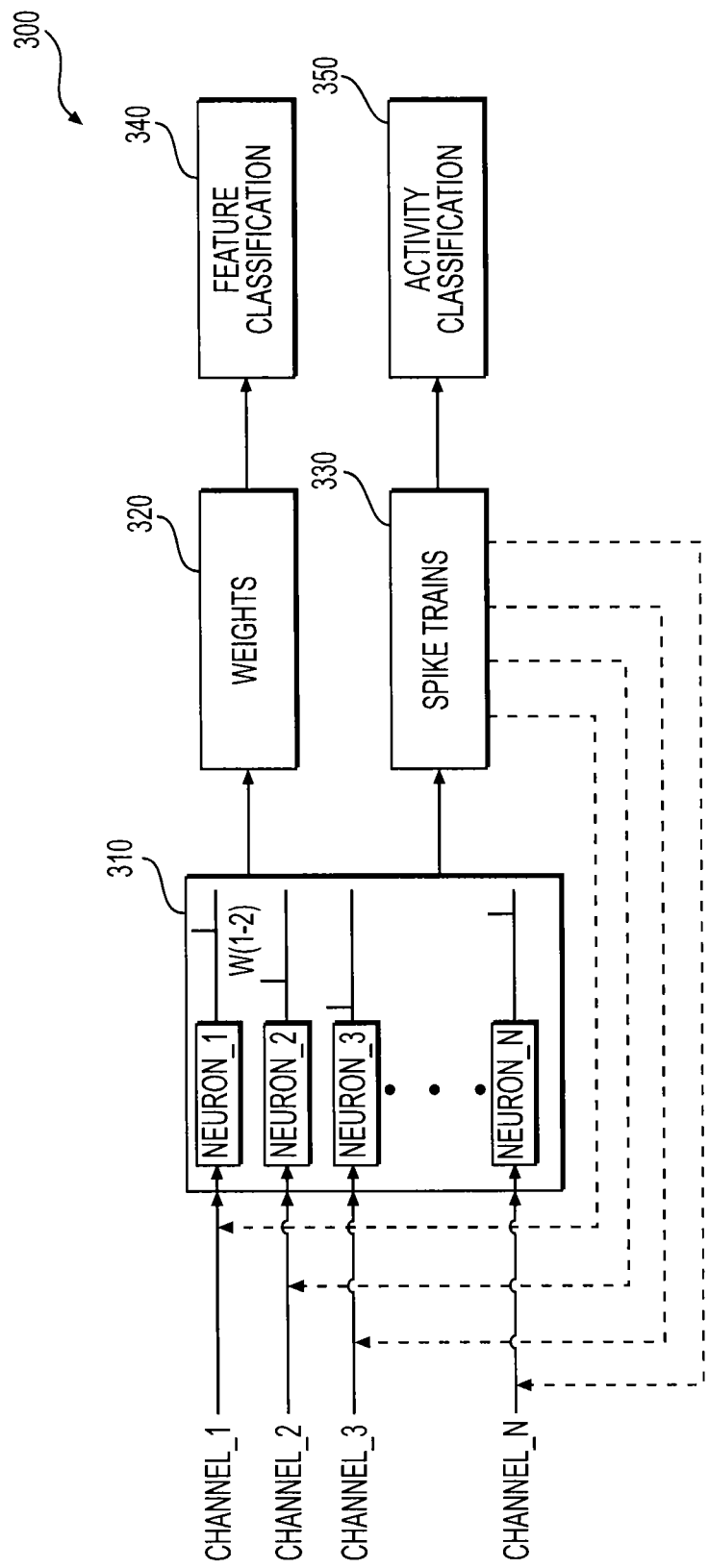
FIG. 3 shows another exemplary data flow 300 according to an embodiment of the disclosure.

FIG. 3 shows another exemplary data flow 300 according to an embodiment of the disclosure. The data flow 300 is similarly configured as the data flow 200 and utilizes certain components that are identical or equivalent to those used in the data flow 200; the description of these components has been provided above and will be omitted here for clarity purposes. However in the FIG. 3 example, the spike trains 330 are feedback to the spiking neural network 310 to form a multiple-layer spiking neural network.

It is also noted that, in an example, a plurality of the spiking neural networks 230 can be serially connected to form a multiple-layer spiking neural network.

Figure 4:
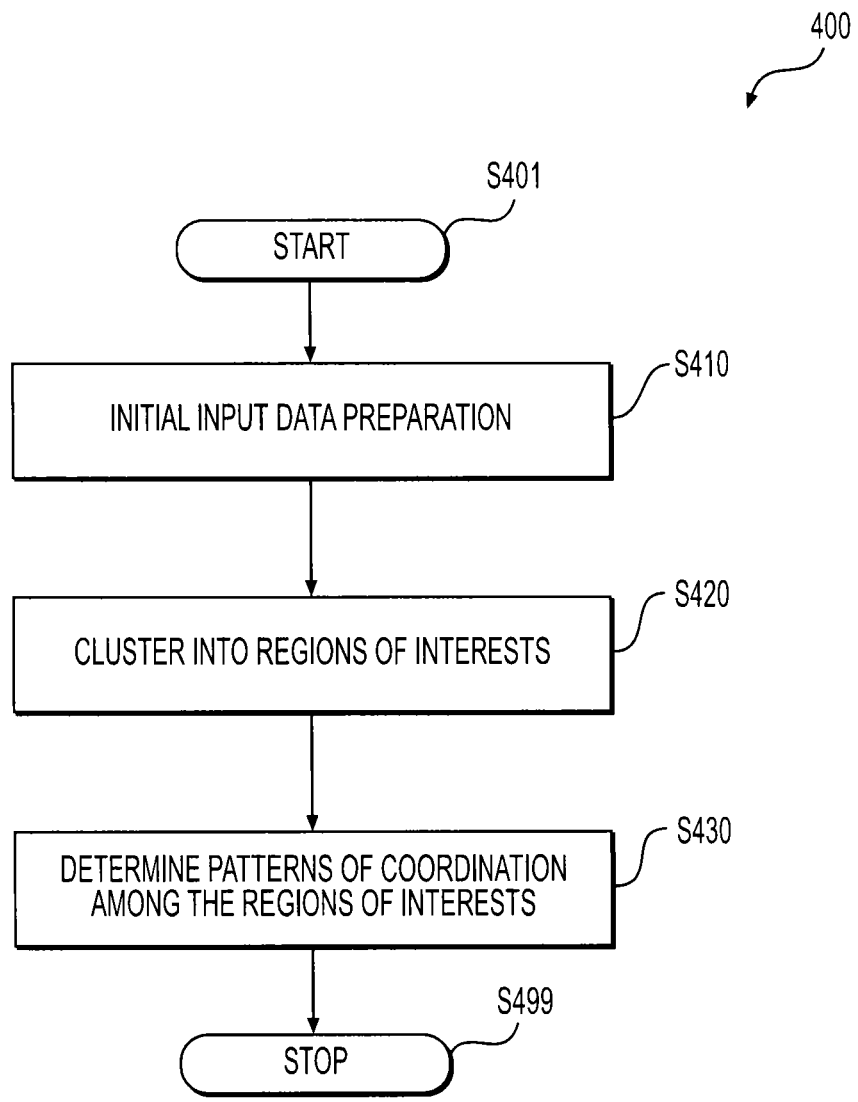
FIG. 4 shows a flow chart outlining an exemplary process 400 according to an embodiment of the disclosure.

FIG. 4 shows a flow chart outlining an exemplary process 400 according to an embodiment of the disclosure. In an example, the process 400 is executed by the system 100. The process starts at S401 and proceeds to S410.

At S410, the input data is initially prepared for analysis. In an example, one or more test subjects are administered fMRI scans at time-domain specific intervals. It is noted that, in an example the test subjects are administrated under a specific function, such as resting, reading, and the like to take the fMRI scans. In an example, for each test subject, 171 samples are recorded over a time duration of five minutes and each sample includes over ~150,000 voxels. The initial data preparation reduces the amount of voxels without losing information fidelity. In an example, a Bayesian regression technique is used, such as disclosed in Applicant's co-pending application Ser. No. 14/167,536, filed Jan. 29, 2014, which is incorporated herein by reference in its entirety.

At S420, the input data is clustered into regions of interests. According to an aspect of the disclosure, many voxels strongly co-vary with their neighbors' activity. Thus, the voxels who co-vary can be clustered into a region of interests. The system 100 can use any suitable technique to cluster voxels. In an example, a correlation-distance based metric is used to cluster voxels.

At S430, patterns of coordination among the regions of interests are determined. In an example, the clustered data forms the input data of the channels in the data flow 200. Then, following the data flow 200, the spiking neuron network 210 generates weights 220 that are indicative of the coordination among the regions of interests. In an example, the test subjects are determined by other techniques as normal without brain injury or with certain level of brain injury. The weights output from the spiking neuron network 210 can be used to setup a baseline for brain injury detection. In an example, the weights from differently labeled test subjects can be used to setup baselines for different levels of brain injuries, such as a baseline for normal without brain injury, a baseline for mild brain injury, a baseline for severe brain injury, and the like. Then, the process proceeds to S499 and terminates.

Figure 5:
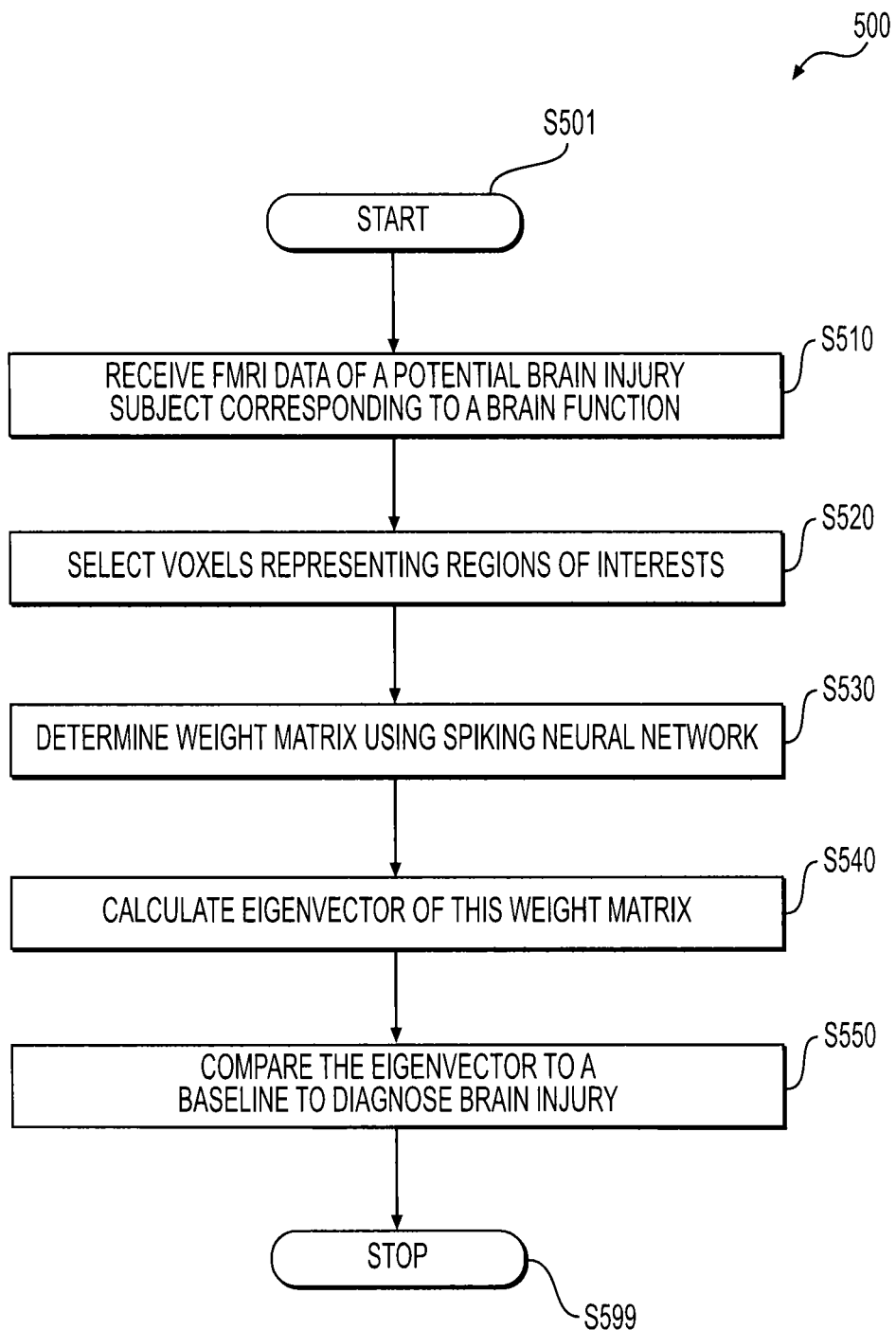
FIG. 5 shows a flow chart outlining an exemplary process 500 according to an embodiment of the disclosure.

FIG. 5 shows a flow chart outlining an exemplary process 500 according to an embodiment of the disclosure. In an example, the process 500 is executed by the system 100 for brain injury detection. The process starts at S501 and proceeds to S510.

At S510, fMRI data of a potential brain injury subject is received. In an example, the potential brain injury subject is administrated under the same specific function as the baselines used for brain injury diagnoses. The fMRI scan generates voxels for the potential brain injury subject.

At S520, voxels that represent the regions of interests are selected. In an example, the selection circuitry 172 selects voxels that represent the regions of interests.

At S530, a weight matrix is determined. In an example, the selected voxels are sent to the data flow 200 via the channels. Then, following the data flow 200, the spiking neuron network 210 generates weights 220 that are indicative of the coordination among the regions of interests for the potential brain injury subject.

At S540, eigenvector of the weight matrix is calculated. In an example, the weight matrix is normalized to a maximum value of unity. In another example, a threshold is determined, and correlation values are compared with the threshold to generate a binary matrix. For example, the number of regions of interests is N, a binary matrix with N by N entries is generated. The binary matrix is similar to an adjacency matrix from graph theory, which describes the connectivity of nodes in a network is generated. Specifically, when a correlation value (e.g., weight) of a first region to a second region is larger than 0.1 for example, a binary "1" is generated in the binary matrix at an entry with a first dimension corresponding to the first region and a second dimension corresponding to the second region; and when the correlation value is equal or smaller than 0.1, a binary "0" is generated in the binary matrix at the entry.

Further, in the example, techniques of spectral graph theory can be applied to the binary matrix. In an example, an eigenvector metric for the binary matrix can be calculated.

At S550, the eigenvector is compared with the baselines to detect the brain injury. According to an aspect of the disclosure, brain injury can cause weaker coordination among the regions of interests. Thus, in an example, when a portion of the eigenvector metric is lower than the baseline of normal subjects, the potential brain injury subject can be a detection of brain injury. In another example, the eigenvector metric can be compared to baselines for different levels of brain injury to determine the level of brain injury. Then the process proceeds to S599 and terminates.

When implemented in hardware, the hardware may comprise one or more of discrete components, an integrated circuit, an application-specific integrated circuit (ASIC), etc.

While aspects of the present disclosure have been described in conjunction with the specific embodiments thereof that are proposed as examples, alternatives, modifications, and variations to the examples may be made. Accordingly, embodiments as set forth herein are intended to be illustrative and not limiting. There are changes that may be made without departing from the scope of the claims set forth below.

What is claimed is:

1. A system for signal processing, comprising:
a selection circuitry that receives data sets sampled at different time from voxels recorded from magnetic resonance imaging (MRI) of a subject and selects a plurality of data units from each data set that corresponds to regions of interests in the data set; and
a coordination detection circuitry including (i) a plurality of channels and (ii) a spiking neural network comprising a plurality of neurons, each channel coupled to a corresponding neuron of the spiking neural network, the coordination detection circuitry receives, via the channels and spiking neural network, the selected data units corresponding to the regions of interests over time, each neuron of the spiking neural network generating a train of spikes based on the received data units over time, the coordination detection circuitry detects a coordination of the regions of interests including the neurons over time, classifies an activity of the subject based on activities of the neurons including at least trains of spikes that are fed back to the spiking neural network for recursively driving the neurons in the spiking neural network, and detects a brain injury of the subject based on the classified activity.

2. The system of claim 1, wherein the selection circuit is configured to receive the voxels from the MRI of the subject when the subject is administrated in a specific function.

3. The system of claim 1, where the coordination detection circuitry is configured to input the plurality of data units at the different time into the spiking neural network to drive neurons in the spiking neural network.

4. The system of claim 3, wherein the spiking neural network outputs a weight matrix for the neurons based on activities of the neurons.

5. The system of claim 4, wherein the coordination detection circuitry is configured to calculate an eigenvector of the weight matrix.

6. The system of claim 5, wherein the coordination detection circuitry is configured to compare a portion of the eigenvector with a baseline to determine a feature of the subject.

7. The system of claim 3, wherein the spiking neural network outputs the trains of spikes indicative of activities of the neurons.

8. The system of claim 7, wherein the trains of spikes are input to another spiking neural network.

9. A method for signal processing, comprising:
receiving, by an interface circuitry, data sets sampled at different time from voxels recorded from magnetic resonance imaging (MRI) of a subject;
selecting, by a selection circuitry, a plurality of data units from each data set, the data units corresponding to regions of interests in the data set;
receiving, by a coordination detection circuitry including (i) a plurality of channels and (ii) a spiking neural network comprising a plurality of neurons, each channel coupled to a corresponding neuron of the spiking neural network, via the channels and spiking neural network, the selected data units corresponding to the regions of interests;
generating, by each neuron of the spiking neural network, a train of spikes based on the received data units over time;
detecting, by the coordination detection circuitry, a coordination of the regions of interests including the neurons over time;
classifying, by the coordination detection circuitry, an activity of the subject based on activities of the neurons including at least trains of spikes;
feeding the trains of spikes back to the spiking neural network to recursively drive the neurons in the spiking neural network; and
detecting, by the coordination detection circuitry, a brain injury of the subject based on the classified activity.

10. The method of claim 9, wherein receiving, by the interface circuitry, the data sets sampled at different time for the subject further comprises:

receiving, by the interface circuitry, voxels from the MRI of the subject administrated in a specific function.

11. The method of claim 9, where detecting, by the coordination detection circuitry, the coordination of the regions of interests over time further comprises:
driving neurons in the spiking neural network with the plurality of data units over the different time.

12. The method of claim 11, further comprising:
updating a weight matrix for correlations of neurons based on the plurality of data units over the different time.

13. The method of claim 12, further comprising:
calculating an eigenvector of the weight matrix.

14. The method of claim 13, further comprising:
comparing a portion of the eigenvector with a baseline to determine a feature of the subject.

15. The method of claim 11, further comprising:
driving the neurons in the spiking neural network to output the trains of spikes indicative of activities of the neurons.

16. The method of claim 15, further comprising:
providing the trains of spikes to another spiking neural network to drive the other spiking neural network.

* * * * *